US012714532B2

(12) United States Patent
Wu et al.

(10) Patent No.: US 12,714,532 B2
(45) **Date of Patent: *Aug. 25, 2026**

(54) SYSTEM AND METHOD FOR FORCE OR TORQUE LIMIT COMPENSATION

(71) Applicant: INTUITIVE SURGICAL OPERATIONS, INC., Sunnyvale, CA (US)

(72) Inventors: Melody Wu, Sunnyvale, CA (US); David W. Weir, San Carlos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 18/650,505

(22) Filed: Apr. 30, 2024

(65) Prior Publication Data

US 2024/0277443 A1 Aug. 22, 2024

Related U.S. Application Data

(63) Continuation of application No. 17/110,944, filed on Dec. 3, 2020, now Pat. No. 11,998,398, which is a (Continued)

(51) Int. Cl.
*A61B 90/00* (2016.01)
*A61B 17/285* (2006.01)
(Continued)

(52) U.S. Cl.
CPC ............ *A61B 90/03* (2016.02); *A61B 17/285* (2013.01); *A61B 17/3205* (2013.01);
(Continued)

(58) Field of Classification Search
CPC ......... A61B 90/00; A61B 90/03; A61B 34/10; A61B 34/32; A61B 34/35; A61B 17/32; A61B 17/3205; A61B 17/285
See application file for complete search history.

(56) References Cited

U.S. PATENT DOCUMENTS 5,048,158 A 9/1991 Koerner
7,061,466 B1 6/2006 Moore et al.
(Continued)

FOREIGN PATENT DOCUMENTS

CN 1200692 A 12/1998
CN 101262829 A 9/2008
(Continued)

OTHER PUBLICATIONS

Extended European Search Report for Application No. EP20159150.0 mailed on Jul. 3, 2020, 7 pages.
(Continued)

*Primary Examiner* — Vi X Nguyen
(74) *Attorney, Agent, or Firm* — Artegis Law Group, LLP

(57) ABSTRACT

Techniques for force and torque limit compensation include a computer-assisted device including a drive unit configured to operate a degree of freedom of an instrument supported by the computer-assisted device and a control unit. The control unit is configured to determine an expected amount of restraining or return to home force or torque applied to the degree of freedom; determine a force or torque limit compensation based on the expected amount of restraining or return to home force or torque; alter one or more force or torque limits based on the force or torque limit compensation; and adjust, using the drive unit, the degree of freedom subject to the one or more altered force or torque limits.

20 Claims, 6 Drawing Sheets

Related U.S. Application Data continuation of application No. 15/573,077, filed as application No. PCT/US2016/032360 on May 13, 2016, now Pat. No. 10,874,474.

(60) Provisional application No. 62/162,239, filed on May 15, 2015.

(51) Int. Cl.

| | |
|---|---|
| ***A61B 17/3205*** | (2006.01) |
| ***A61B 18/08*** | (2006.01) |
| ***A61B 34/00*** | (2016.01) |
| ***A61B 34/10*** | (2016.01) |
| ***A61B 34/20*** | (2016.01) |
| ***A61B 34/32*** | (2016.01) |
| ***A61B 34/35*** | (2016.01) |
| ***B25J 9/16*** | (2006.01) |
| *A61B 17/00* | (2006.01) |
| *A61B 17/072* | (2006.01) |
| *A61B 18/14* | (2006.01) |
| *A61B 34/30* | (2016.01) |

(52) U.S. Cl.

CPC ............ *A61B 18/085* (2013.01); *A61B 34/00* (2016.02); *A61B 34/10* (2016.02); *A61B 34/20* (2016.02); *A61B 34/32* (2016.02); *A61B 34/35* (2016.02); *B25J 9/163* (2013.01); *B25J 9/1633* (2013.01); *A61B 2017/003* (2013.01); *A61B 2017/07285* (2013.01); *A61B 18/1445* (2013.01); *A61B 2018/1455* (2013.01); *A61B 2034/102* (2016.02); *A61B 2034/306* (2016.02); *A61B 34/71* (2016.02); *A61B 2090/031* (2016.02)

(56) References Cited

U.S. PATENT DOCUMENTS

| | | | | |
|---|---|---|---|---|
| 9,014,856 | B2 | 4/2015 | Manzo et al. | |
| 9,522,003 | B2 | 12/2016 | Weir et al. | |
| 10,874,474 | B2 * | 12/2020 | Wu ........................ | A61B 34/30 |
| 11,998,398 | B2 * | 6/2024 | Wu ........................ | A61B 34/00 |
| 2004/0138530 | A1 | 7/2004 | Kawai et al. | |
| 2007/0142823 | A1 | 6/2007 | Prisco et al. | |
| 2008/0046122 | A1 | 2/2008 | Manzo et al. | |
| 2010/0094312 | A1 | 4/2010 | Ruiz et al. | |
| 2010/0270355 | A1 | 10/2010 | Whitman et al. | |
| 2011/0288573 | A1 | 11/2011 | Yates et al. | |
| 2012/0046522 | A1 | 2/2012 | Naito | |
| 2012/0215220 | A1 | 8/2012 | Manzo et al. | |
| 2014/0052152 | A1 * | 2/2014 | Au ........................ | A61B 34/37 606/130 |
| 2014/0052298 | A1 | 2/2014 | Hourtash et al. | |
| 2014/0200596 | A1 | 7/2014 | Weir et al. | |
| 2014/0200851 | A1 | 7/2014 | Weir et al. | |
| 2015/0051733 | A1 | 2/2015 | Nowlin et al. | |
| 2015/0119638 | A1 * | 4/2015 | Yu ........................ | A61B 90/30 600/102 |
| 2016/0136810 | A1 | 5/2016 | Wakai et al. | |
| 2017/0179857 | A1 | 6/2017 | Liao et al. | |
| 2021/0085419 | A1 | 3/2021 | Wu et al. | |

FOREIGN PATENT DOCUMENTS

| | | | |
|---|---|---|---|
| CN | 101507627 | A | 8/2009 |
| CN | 101940092 | A | 1/2011 |
| CN | 102405019 | A | 4/2012 |
| CN | 102770060 | A | 11/2012 |
| EP | 1306792 | A2 | 5/2003 |
| EP | 2639020 | A2 | 9/2013 |
| JP | 2004041538 | A | 2/2004 |
| JP | 2007089808 | A | 4/2007 |
| JP | 5048158 | B2 | 10/2012 |
| JP | 2013163224 | A | 8/2013 |
| KR | 20130108367 | A | 10/2013 |
| WO | WO-2007111737 | A2 | 10/2007 |
| WO | WO-2014110561 | A1 | 7/2014 |
| WO | WO-2014110564 | A1 | 7/2014 |
| WO | WO-2015012242 | A1 | 1/2015 |
| WO | WO-2016149279 | A1 | 9/2016 |

OTHER PUBLICATIONS

Extended European Search Report for Application No. EP16797008.6 mailed on Dec. 6, 2018, 8 pages.

Extended European Search Report for Application No. EP23194251.7, mailed on Nov. 29, 2023, 06 pages.

International Search Report and Written Opinion for Application No. PCT/US2016/032360, mailed on Aug. 19, 2016, 11 pages.

Office Action mailed Oct. 31, 2019 for Chinese Application No. 201680028074 filed May 13, 2016, 32 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

| DOF Position | $X_0$ | $X_1$ | $X_2$ | $X_3$ | $X_4$ |
|---|---|---|---|---|---|
| Torque Limit Compensation | 0 | 0 | $T_1$ | $T_2$ | $T_2$ |

SYSTEM AND METHOD FOR FORCE OR TORQUE LIMIT COMPENSATION

RELATED APPLICATIONS

This patent application is a continuation of U.S. patent application Ser. No. 17/110,944 (filed on Dec. 3, 2020), which is a continuation of U.S. patent application Ser. No. 15/573,077 (filed on Nov. 9, 2017), which is a U.S. National Stage patent application of International Patent Application No. PCT/US2016/032360 (filed on May 13, 2016), the benefit of which is claimed, and claims priority to and the benefit of the filing date of U.S. Provisional Patent Application 62/162,239, entitled "SYSTEM AND METHOD FOR FORCE OR TORQUE LIMIT COMPENSATION" and filed May 15, 2015. Each of these related applications is incorporated by reference herein in its entirety.

TECHNICAL FIELD

The present disclosure relates generally to operation of devices with articulated arms and end effectors and more particularly to force or torque limit compensation in end effectors.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

Minimally invasive surgical techniques using computer-assisted medical devices generally attempt to perform surgical and/or other procedures while minimizing damage to healthy tissue. Some minimally invasive procedures may be performed remotely through the use of computer-assisted medical devices with surgical instruments. With many computer-assisted medical devices, a surgeon and/or other medical personnel may typically manipulate input devices using one or more controls on an operator console. As the surgeon and/or other medical personnel operate the various controls at the operator console, the commands are relayed from the operator console to a patient side device to which one or more end effectors and/or surgical instruments are mounted. In this way, the surgeon and/or other medical personnel are able to perform one or more procedures on a patient using the end effectors and/or surgical instruments. Depending upon the desired procedure and/or the surgical instruments in use, the desired procedure may be performed partially or wholly under control of the surgeon and/or medical personnel using telcoperation and/or under semi-autonomous control where the surgical instrument may perform a sequence of operations based on one or more activation actions by the surgeon and/or other medical personnel.

Minimally invasive surgical instruments, whether actuated manually, teleoperatively, and/or semi-autonomously may be used in a variety of operations and/or procedures and may have various configurations. Many such instruments include an end effector mounted at a distal end of a shaft that may be mounted to the distal end of an articulated arm. In many operational scenarios, the shaft may be configured to be inserted (e.g., laparoscopically, thorascopically, and/or the like) through an opening (e.g., a body wall incision, a natural orifice, and/or the like) to reach a remote surgical site. In some instruments, an articulating wrist mechanism may be mounted to the distal end of the instrument's shaft to support the end effector with the articulating wrist providing the ability to alter an orientation of the end effector relative to a longitudinal axis of the shaft.

End effectors of different design and/or configuration may be used to perform different tasks, procedures, and functions so as to be allow the surgeon and/or other medical personnel to perform any of a variety of surgical procedures. Examples include, but are not limited to, cauterizing, ablating, suturing, cutting, stapling, fusing, scaling, etc., and/or combinations thereof. Accordingly, end effectors can include a variety of components and/or combinations of components to perform these surgical procedures.

Consistent with the goals of a minimally invasive procedure, the size of the end effector is typically kept as small as possible while still allowing it to perform its intended task. One approach to keeping the size of the end effector small is to accomplish actuation of the end effector through the use of one or more inputs at a proximal end of the surgical instrument, which is typically located externally to the patient. Various gears, levers, pulleys, cables, rods, bands, and/or the like, may then be used to transmit actions from the one or more inputs along the shaft of the surgical instrument and to actuate the end effector. In the case of a computer-assisted medical device with an appropriate surgical instrument, a transmission mechanism at the proximal end of the instrument interfaces with various motors, solenoids, servos, active actuators, hydraulics, pneumatics, and/or the like provided on an articulated arm of the patient side device or a patient side cart. The motors, solenoids, servos, active actuators, hydraulics, pneumatics, and/or the like typically receive control signals through a master controller and provide input in the form of force and/or torque at the proximal end of the transmission mechanism, which the various gears, levers, pulleys, cables, rods, bands, and/or the like ultimately transmit to actuate the end effector at the distal end of the transmission mechanism.

It is often desirable for one or more of the degrees of freedom of an end effector to be configured with a default or home position that, in the absence of active actuation, the one or more degrees of freedom are expected to return to. In some examples, safety concerns may dictate that a sharp cutting blade of an end effector be returned to a sheathed and/or garaged home position when the cutting blade is not being used. This may reduce the likelihood that tissue of a patient and/or medical personnel handling the end effector will be accidentally cut by the cutting blade. In some examples, other of the degrees of freedom may have home positions to satisfy other design and/or safety concerns. In some examples, the surgical instrument and/or the end effector may be configured with a restraining and/or return to home mechanism that applies force and/or torque to the degree of freedom to return the degree of freedom to the home position. In some examples, this restraining and/or return to home mechanism may negatively impact use of the end effector as the restraining and/or return to home mechanism may have to be overcome in order to operate the respective degree of freedom as desired.

Accordingly, improved methods and systems for the operation of surgical instruments, such as a cutting instrument, are desirable. In some examples, it may be desirable to include restraining and/or return to home mechanisms that support a return to home function, yet do not otherwise negatively impact use of a surgical instrument.

SUMMARY

Consistent with some embodiments, a surgical instrument for use with a computer-assisted medical device includes an end effector located at a distal end of the instrument, a drive unit for operating a degree of freedom of the instrument, a shaft coupled to the drive unit, and one or more drive mechanisms in the shaft for coupling force or torque from the drive unit to the end effector and the articulated wrist. To control the degree of freedom, the instrument is configured to determine a current position of the degree of freedom, determine a force or torque limit compensation based on the current position, alter one or more force or torque limits based on the force or torque limit compensation, and adjust the degree of freedom subject to the one or more force or torque limits.

Consistent with some embodiments, a method of operating a surgical instrument for use with a computer-assisted medical device includes determining a current position of a degree of freedom of the surgical instrument, determining a force or torque limit compensation based on the current position, altering one or more force or torque limits based on the force or torque limit compensation, and adjusting the degree of freedom subject to the one or more force or torque limits.

Consistent with some embodiments, a non-transitory machine-readable medium includes a plurality of machine-readable instructions which when executed by one or more processors associated with a computer-assisted medical device are adapted to cause the one or more processors to perform a method. The method includes determining a current position of a degree of freedom of a surgical instrument operated by the computer-assisted medical device, determining a force or torque limit compensation based on the current position, altering one or more force or torque limits based on the force or torque limit compensation, and adjusting the degree of freedom subject to the one or more force or torque limits.

Consistent with some embodiments, a computer-assisted medical device includes one or more processors, an articulated arm, and a surgical instrument coupled to a distal end of the articulated arm. The surgical instrument includes an end effector located at a distal end of the surgical instrument, a drive unit located at a proximal end of the surgical instrument for operating a degree of freedom of the surgical instrument, a shaft coupled to the drive unit, and one or more drive mechanisms in the shaft for coupling force or torque from the drive unit to the end effector and the articulated wrist. The computer-assisted medical device is configured to determine a current position of the degree of freedom, determine a force or torque limit compensation based on the current position, alter one or more force or torque limits based on the force or torque limit compensation, and adjust the degree of freedom subject to the one or more force or torque limits.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
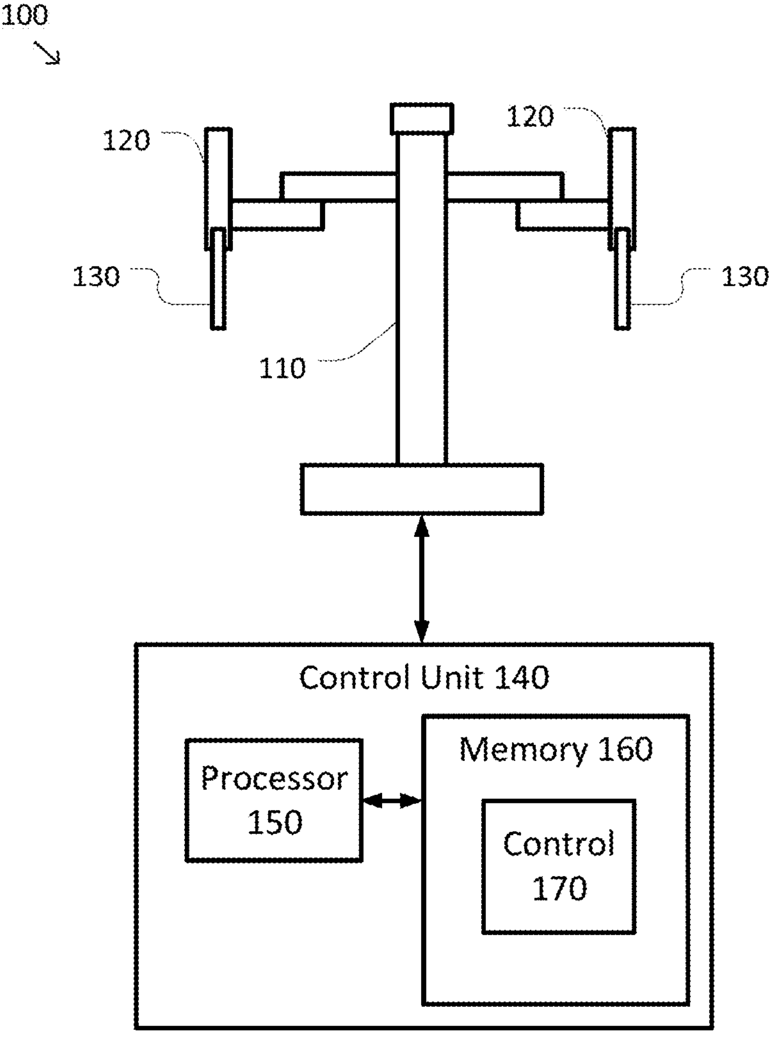
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a computer-assisted device 110 with one or more movable or articulated arms 120. Each of the one or more articulated arms 120 may support one or more instruments 130. In some examples, computer-assisted device 110 may be consistent with a computer-assisted surgical device. The one or more articulated arms 120 may each provide support for medical instruments 130 such as surgical instruments, imaging devices, and/or the like. In some examples, the instruments 130 may include end effectors that are capable of, but are not limited to, performing, gripping, retracting, cauterizing, ablating, suturing, cutting, stapling, fusing, sealing, etc., and/or combinations thereof.

Computer-assisted device 110 may further be coupled to an operator workstation (not shown), which may include one or more master controls for operating the computer-assisted device 110, the one or more articulated arms 120, and/or the instruments 130. In some examples, the one or more master controls may include master manipulators, levers, pedals, switches, keys, knobs, triggers, and/or the like. In some embodiments, computer-assisted device 110 and the operator workstation may correspond to a da Vinci® Surgical System commercialized by Intuitive Surgical, Inc. of Sunnyvale, California. In some embodiments, computer-assisted surgical devices with other configurations, fewer or more articulated arms, and/or the like may be used with computer-assisted system 100.

Computer-assisted device 110 is coupled to a control unit 140 via an interface. The interface may include one or more cables, fibers, connectors, and/or buses and may further include one or more networks with one or more network switching and/or routing devices. Control unit 140 includes a processor 150 coupled to memory 160. Operation of control unit 140 is controlled by processor 150. And although control unit 140 is shown with only one processor 150, it is understood that processor 150 may be representative of one or more central processing units, multi-core processors, microprocessors, microcontrollers, digital signal processors, field programmable gate arrays (FPGAs), application specific integrated circuits (ASICs), and/or the like in control unit 140. Control unit 140 may be implemented as a stand-alone subsystem and/or board added to a computing device or as a virtual machine. In some embodiments, control unit 140 may be included as part of the operator workstation and/or operated separately from, but in coordination with the operator workstation.

Memory 160 may be used to store software executed by control unit 140 and/or one or more data structures used during operation of control unit 140. Memory 160 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown in FIG. 1, memory 160 includes a control application 170 that may be used to support autonomous, semiautonomous, and/or teleoperated control of computer-assisted device 110. Control application 170 may include one or more application programming interfaces (APIs) for receiving position, motion, force, torque, and/or other sensor information from computer-assisted device 110, articulated arms 120, and/or instruments 130, exchanging position, motion, force, torque, and/or collision avoidance information with other control units regarding other devices, and/or planning and/or assisting in the planning of motion for computer-assisted device 110, articulated arms 120, and/or instruments 130. In some examples, control application 170 may further support autonomous, semiautonomous, and/or teleoperated control of the instruments 130 during a surgical procedure. And although control application 170 is depicted as a software application, control application 170 may be implemented using hardware, software, and/or a combination of hardware and software.

In some embodiments, computer-assisted system 100 may be found in an operating room and/or an interventional suite. And although computer-assisted system 100 includes only one computer-assisted device 110 with two articulated arms 120 and corresponding instruments 130, one of ordinary skill would understand that computer-assisted system 100 may include any number of computer-assisted devices with articulated arms and/or instruments of similar and/or different in design from computer-assisted device 110. In some examples, each of the computer-assisted devices may include fewer or more articulated arms and/or instruments.

Figure 2:
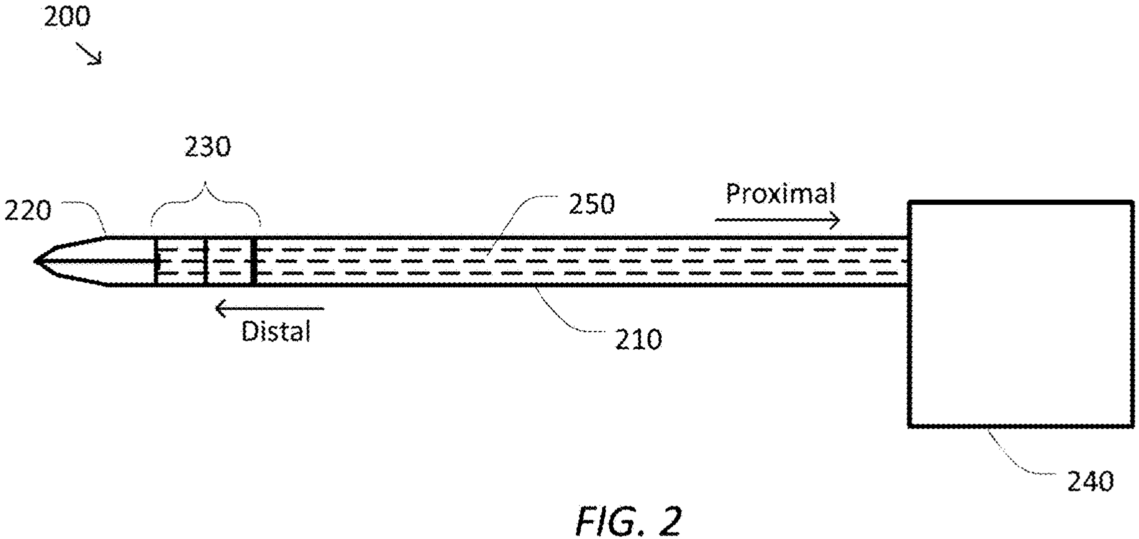
FIG. 2 is a simplified diagram showing a minimally invasive surgical instrument according to some embodiments.

FIG. 2 is a simplified diagram showing a minimally invasive surgical instrument 200 according to some embodiments. In some embodiments, surgical instrument 200 may be consistent with any of the instruments 130 of FIG. 1. The directions "proximal" and "distal" as depicted in FIG. 2 and as used herein help describe the relative orientation and location of components of surgical instrument 200. Distal generally refers to elements in a direction further along a kinematic chain from a base of a computer-assisted device, such as computer-assisted device 110, and/or or closest to the surgical work site in the intended operational use of the surgical instrument 200. Proximal generally refers to elements in a direction closer along a kinematic chain toward the base of the computer-assisted device and/or one of the articulated arms of the computer-assisted device.

As shown in FIG. 2, surgical instrument 200 includes a long shaft 210 used to couple an end effector 220 located at a distal end of shaft 210 to where the surgical instrument 200 is mounted to an articulated arm and/or a computer-assisted device at a proximal end of shaft 210. Depending upon the particular procedure for which the surgical instrument 200 is being used, shaft 210 may be inserted through an opening (e.g., a body wall incision, a natural orifice, and/or the like) in order to place end effector 220 in proximity to a remote surgical site located within the anatomy of a patient. As further shown in FIG. 2, end effector 220 is generally consistent with a two-jawed gripper-style end effector, which in some embodiments may further include a cutting and/or a fusing or sealing mechanism as is described in further detail below with respect to FIGS. 3 and 4A-4C. However, one of ordinary skill would understand that different surgical instruments 200 with different end effectors 220 are possible and may be consistent with the embodiments of surgical instrument 200 as described elsewhere herein.

A surgical instrument, such as surgical instrument 200 with end effector 220 typically relies on multiple degrees of freedom (DOFs) during its operation. Depending upon the configuration of surgical instrument 200 and the articulated arm and/or computer-assisted device to which it is mounted, various DOFs that may be used to position, orient, and/or operate end effector 220 are possible. In some examples, shaft 210 may be inserted in a distal direction and/or retreated in a proximal direction to provide an insertion DOF that may be used to control how deep within the anatomy of the patient that end effector 220 is placed. In some examples, shaft 210 may be able rotate about its longitudinal axis to provide a roll DOF that may be used to rotate end effector 220. In some examples, additional flexibility in the position and/or orientation of end effector 220 may be provided by an articulated wrist 230 that is used to couple end effector 220 to the distal end of shaft 210. In some examples, articulated wrist 230 may include one or more rotational joints, such as one or more roll, pitch or yaw joints that may provide one or more "roll," "pitch," and "yaw" DOF(s), respectively, that may be used to control an orientation of end effector 220 relative to the longitudinal axis of shaft 210. In some examples, the one or more rotational joints may include a pitch and a yaw joint; a roll, a pitch, and a yaw joint, a roll, a pitch, and a roll joint; and/or the like. In some examples, end effector 220 may further include a grip DOF used to control the opening and closing of the jaws of end effector 220 and/or an activation DOF used to control the extension, retraction, and/or operation of a cutting mechanism as is described in further detail below.

Surgical instrument 200 further includes a drive system 240 located at the proximal end of shaft 210. Drive system 240 includes one or more components for introducing forces and/or torques to surgical instrument 200 that may be used to manipulate the various DOFs supported by surgical instrument 200. In some examples, drive system 240 may include one or more motors, solenoids, servos, active actuators, hydraulic actuators, pneumatic actuators, and/or the like that are operated based on signals received from a control unit, such as control unit 140 of FIG. 1. In some examples, the signals may include one or more currents, voltages, pulse-width modulated wave forms, and/or the like. In some examples, drive system 240 may include one or more shafts, gears, pulleys, rods, bands, and/or the like which may be coupled to corresponding motors, solenoids, servos, active actuators, hydraulics, pneumatics, and/or the like that are part of the articulated arm, such as any of the articulated arms 120, to which surgical instrument 200 is mounted. In some examples, the one or more drive inputs, such as shafts, gears, pulleys, rods, bands, and/or the like, may be used to receive forces and/or torques from the motors, solenoids, servos, active actuators, hydraulics, pneumatics, and/or the like and apply those forces and/or torques to adjust the various DOFs of surgical instrument 200.

In some embodiments, the forces and/or torques generated by and/or received by drive system 240 may be transferred from drive system 240 and along shaft 210 to the various joints and/or elements of surgical instrument 200 located distal to drive system 240 using one or more drive mechanisms 250. In some examples, the one or more drive mechanisms 250 may include one or more gears, levers, pulleys, cables, rods, bands, and/or the like. In some examples, shaft 210 is hollow and the drive mechanisms 250 pass along the inside of shaft 210 from drive system 240 to the corresponding DOF in end effector 220 and/or articulated wrist 230. In some examples, each of the drive mechanisms 250 may be a cable disposed inside a hollow sheath or lumen in a Bowden cable like configuration. In some examples, the cable and/or the inside of the lumen may be coated with a low-friction coating such as polytetrafluoroethylene (PTFE) and/or the like. In some examples, as the proximal end of each of the cables is pulled and/or pushed inside drive system 240, such as by wrapping and/or unwrapping the cable about a capstan or shaft, the distal end of the cable moves accordingly and applies a suitable force and/or torque to adjust one of the DOFs of end effector 220, articulated wrist 230, and/or surgical instrument 200.

Figure 3:
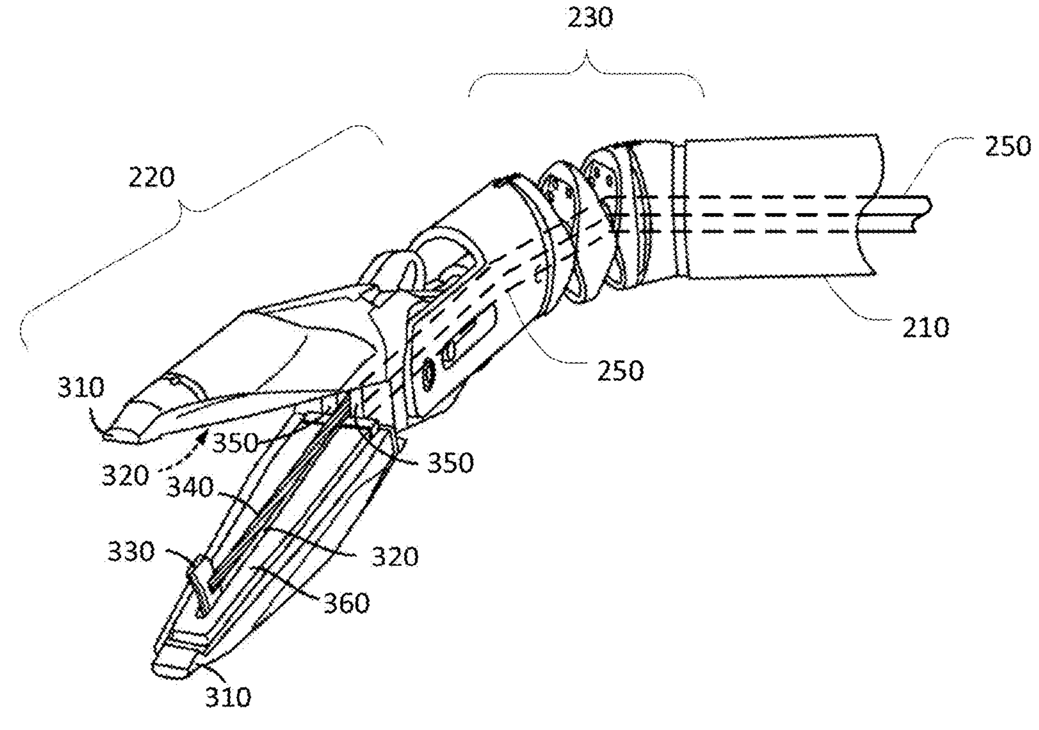
FIG. 3 is a simplified perspective diagram of the distal end of the surgical instrument of FIG. 2 according to some embodiments.

FIG. 3 is a simplified perspective diagram of the distal end of surgical instrument 200 according to some embodiments. As shown in FIG. 3, the distal end of surgical instrument 200 is depicted so as to show additional details of end effector 220, articulated wrist 230, and drive mechanisms 250. In more detail, end effector 220 includes opposing jaws 310 shown in an open position. Jaws 310 are configured to move between open and closed positions so that end effector 220 may be used during a procedure to grip and release tissue and/or other structures, such as sutures, located at the surgical site. In some examples, jaws 310 may be operated together as a single unit with both jaws 310 opening and/or closing at the same time. In some examples, jaws 310 may be opened and/or closed independently so that, for example, one jaw 310 could be held steady which the other jaw 310 may be opened and/or closed.

Figure 4A:
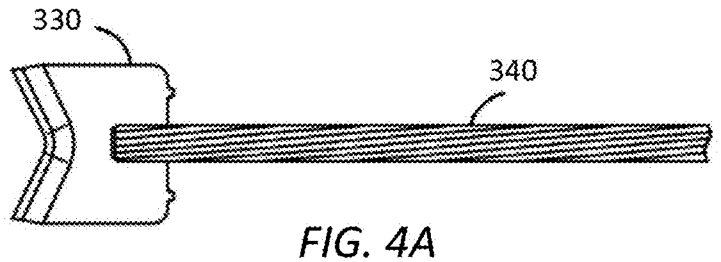
FIGS. 4A-4C are simplified cut-away diagrams of the end effector of FIGS. 2 and 3 according to some embodiments.
Figure 4B:
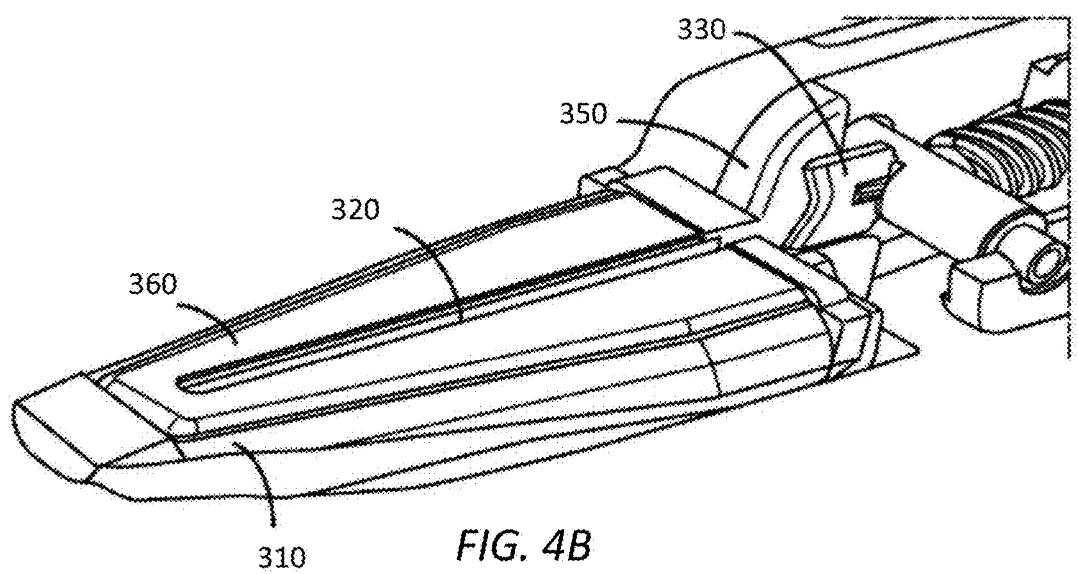
Figure 4C:
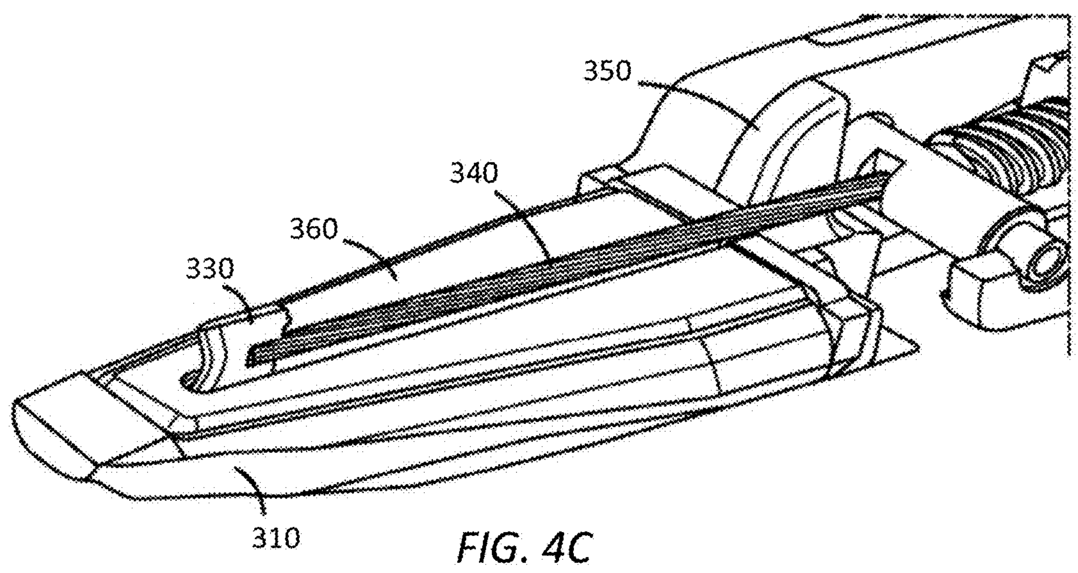

FIG. 3 shows that a gripping surface on an inside of each of jaws 310 includes a corresponding groove 320, which may act as a guide for a cutting blade 330, although the groove 320 may be omitted from one or more of jaws 310. As cutting blade 330 is extended toward the distal end of end effector 220 and/or retracted toward the proximal end of end effector 220, each of the grooves 320 may aid in the alignment and/or positioning of cutting blade 330 during a cutting operation. Extraction and/or retraction of cutting blade 330 is accomplished using a drive component 340 to which cutting blade 330 is attached. In some examples, drive component 340 pushes on cutting blade 330 to extend cutting blade 330 and pulls on cutting blade 330 to retract cutting blade 330. Use and positioning of cutting blade 330 is shown in FIGS. 4A-4C, which are simplified cut-away diagrams of end effector 220 according to some embodiments. FIG. 4A shows the relationship between cutting blade 330 and drive component 340.

End effector 220 further includes a garage feature 350 located at a proximal end of jaws 310. Garage feature 350 includes an opening through which both drive component 340 and cutting blade 330 may pass. Garage feature 350 is configured to provide a safe storage area for cutting blade 330 when cutting blade 330 is not in use. Thus, when cutting blade 330 is not actively being used as part of a cutting operation, end effector 220 is configured so that cutting blade 330 may be retracted into garage feature 350 in a "garaged" or stored position in which cutting blade 330 is recessed proximally behind jaws 310 as shown in FIG. 4B. Cutting blade 330 may additionally be extended to a position in which cutting blade 330 is positioned at or near a distal end of one of the grooves 320 as shown in FIG. 4C. In some examples, the positioning of cutting blade 330 as shown in FIG. 4C may correspond to a position of cutting blade 330 during a cutting operation.

In some examples, end effector 220 and surgical instrument 200 are designed so that the default or home position of cutting blade 330 is within garage feature 350. This arrangement of garage feature 350 may provide several features to end effector 220. In some examples, when cutting blade 330 is retracted into garage feature 350, the sharp cutting edge of cutting blade 330 is effectively sheathed so that cutting blade 330 is unlikely to accidentally cut tissue during a procedure and/or medical personnel handling surgical instrument 200 and/or end effector 220 before and/or after a procedure. In some examples, when cutting blade 330 is retracted into garage feature 350, cutting blade 330 may also be protected from damage, such as accidental dulling, when cutting blade 330 is not actively being used to cut.

Referring back to FIG. 3, in some embodiments, the gripping surface on the inside of each of jaws 310 may further include one or more optional electrodes 360. In some examples, electrodes 360 may be used to deliver electrosurgical energy to fuse tissue being held between jaws 310. In some examples, electrodes 360 may provide an electrocautery, fusing, and/or scaling feature to end effector 220 so that tissue may be cut and/or fused/sealed using the same surgical tool 200.

In some embodiments, operation of jaws 310, cutting blade 330, and/or the joints of articulated wrist 230 may be accomplished using corresponding ones of the drive mechanisms 250. In some examples, when jaws 310 are operated independently, a distal end of two of the drive mechanisms 250 (one for each of jaws 310) may be coupled to a respective jaw 310 so that as the corresponding drive mechanism 250 applies a pull and/or a pushing force (for example, using a cable, lead screw, and/or the like), the respective jaw 310 may be opened and/or closed. In some examples, when jaws 310 are operated together, both jaws 310 may be coupled to the distal end of the same drive mechanism 250. In some examples, drive component 340 may be coupled to a distal end of a corresponding drive mechanism 250 so that forces and/or torques applied to the corresponding drive mechanism 250 may be transferred to the push and/or pull motion of drive component 340. In some examples, additional drive mechanisms 350 may be used to operate the roll, pitch, and/or yaw in articulated wrist 230.

Figure 5:
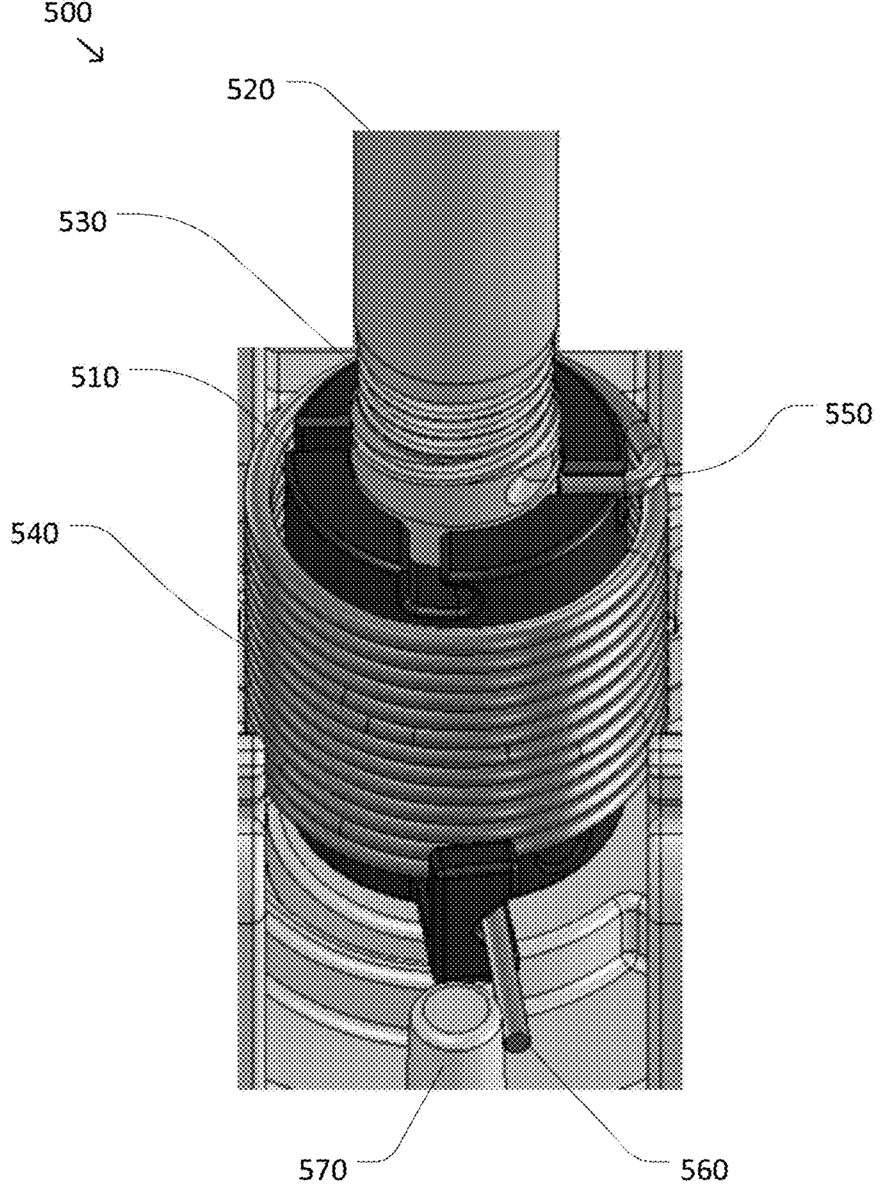
FIG. 5 is a simplified perspective diagram of a drive unit for a degree of freedom according to some embodiments.

FIG. 5 is a simplified perspective diagram of a drive unit 500 for a degree of freedom according to some embodiments. According to some embodiments, drive unit 500 may be representative of a portion of the components in drive system 240 of FIG. 2. As shown in FIG. 5, drive unit 500 is based on a rotational actuation approach in which a capstan 510 is rotated to actuate a DOF. Capstan 510 is coupled to a drive shaft 520 which may be the drive shaft of a motor, servo, active actuator, hydraulic actuator, pneumatic actuator, and/or the like (not shown). As torque is applied to drive shaft 520 and drive shaft 520 and capstan 510 are rotated, a cable 530 attached to capstan 510 and/or drive shaft 520 may be further wrapped around and/or unwrapped from around capstan 510 and/or drive shaft 520. When cable 530 is attached to the proximal end of a corresponding drive mechanism, such as any of drive mechanisms 250, the wrapping and unwrapping of the cable may translate into corresponding pulling and pushing forces and/or torques that may be applied to a DOF of an end effector located at the distal end of the drive mechanism. In some examples, rotation of capstan 510 and drive shaft 520 and the corresponding wrapping and/or unwrapping of cable 530 may result in opening and/or closing of gripper jaws such as jaws 310, extending and/or retracting of a cutting blade such as cutting blade 330, flexing and/or unflexing of articulated wrist joints, and/or the like. In some examples, monitoring a rotation angle and/or rotational velocity of capstan 510 and/or drive shaft 520 may also provide an indication of a current position and/or velocity of the corresponding DOF coupled to cable 530 through the corresponding drive mechanism. Thus, when drive unit 500 is used in conjunction with the DOFs of surgical instrument 200, the rotation angle and/or rotational velocity of capstan 510 and/or drive shaft 520 may provide useful feedback on the angle to which jaws 310 are opened, the position of cutting blade 330, and/or the pitch and/or yaw angle of articulated wrist 230 depending on which of the drive mechanisms 250 cable 530 is coupled.

Because it is often desirable for a DOF in an end effector to be configured with a default, rest, and/or home position when the DOF is not being actuated, in some embodiments a drive unit, such as drive unit 500 may include some type of resistive and/or restraining mechanism to return drive unit 500 to a corresponding home position. In some examples, use of a home position for a DOF may support configuration of a surgical instrument, such as surgical instrument 200, where gripping jaws are automatically closed and/or mostly closed, cutting blades are retracted into a garage feature, articulated wrist joints are straightened, and/or the like. As shown in FIG. 5, drive unit 500 includes a restraining mechanism in the form of a torsion spring 540. Torsion spring 540 is shown attached at one end 550 to capstan 510 and wrapped around capstan 510. As capstan 510 is rotated, a second end 560 of torsion spring 540 may freely rotate until it rotates up against a stop 570 that may be part of a body of drive unit 500. As capstan 510 continues to rotate after the second end 560 of torsion spring 540 is against stop 570, torsion spring 540 will begin to provide a restraining and/or return to home force and/or torque to capstan 510 as dictated by the amount of rotation of capstan 510 and a spring constant of torsion spring 540. Thus, as greater amounts of rotation are applied to capstan 510, torsion spring 540 applies increasing return to home force and/or torque to capstan 510. It is this return to home force and/or torque on capstan 510 that may be used, for example, to close the gripping jaws, retract the cutting blade, and/or straighten the articulated wrist joints.

Although FIG. 5 shows the restraining mechanism as a torsion spring wrapped around capstan 510, one of ordinary skill would recognize other possible restraining mechanisms and/or configurations for the restraining mechanisms to accomplish a similar restraining/return to home function. In some examples, the body of drive unit 500 may further include a second stop to provide a return to home force and/or torque to capstan 510 in an opposite direction to the return to home force and/or torque resulting from stop 570. In some examples, the second end 560 of torsion spring 540 may be mounted to the body of drive unit 500 so that no free movement of torsion spring 540 is permitted before torsion spring 540 begins applying return to home force and/or torque to capstan 510 and/or torsion spring 540 applies at least some return to home force and/or torque to capstan 510 even without rotation of capstan 510.

According to some embodiments, selection of an appropriately sized restraining mechanism, such as the spring constant for torsion spring 540, for a DOF of an end effector may present several challenges to the designer of a surgical instrument. In some situations it may be desirable to select the size of the restraining mechanism to overcome any likely and/or reasonable interference with the desired return to home function of the corresponding drive unit of the DOF. In some examples, selection of the size of the restraining mechanism to overcome any likely and/or reasonable interference tends to oversize the restraining mechanism for many of the possible operational scenarios. Additionally, as the size of the restraining mechanism increases and/or the amount of restraining and/or return to home force and/or torque applied is increased with increased deviation from the home position, the amount of restraining and/or return to home force and/or torque may negatively impact the ability of the drive unit to operate the DOF. In some examples, this may result in a smaller operational margin for the DOF that results in less force and/or torque being available to drive the DOF to perform an operation. For example, less cutting force and/or torque may be available to apply to a cutting blade to perform a cut. In some examples, one solution is to increase the size of the motor, solenoid, servo, active actuator, hydraulic actuator, pneumatic actuator, and/or the like coupled to the drive unit and to adjust force and/or torque limits on the motor, solenoid, servo, active actuator, hydraulic actuator, pneumatic actuator, and/or the like to compensate for the largest possible restraining and/or return to home force and/or torque that may have to be overcome. In some examples, such an increase in force and/or torque limits may not be consistent with certain modes of operation of the DOF or the surgical instrument. In addition, the increased force and/or torque limits may result in operation of the DOF that results in increased stress and/or strain placed on the drive mechanism that may also result in increased wear on the drive mechanism, stretching of the drive mechanism, and/or the like. In some examples, the stretching of the drive mechanism may result in the drive mechanism and the corresponding DOF becoming out of tolerance, thus resulting is a diminished ability to control the DOF as desired.

Figure 6:
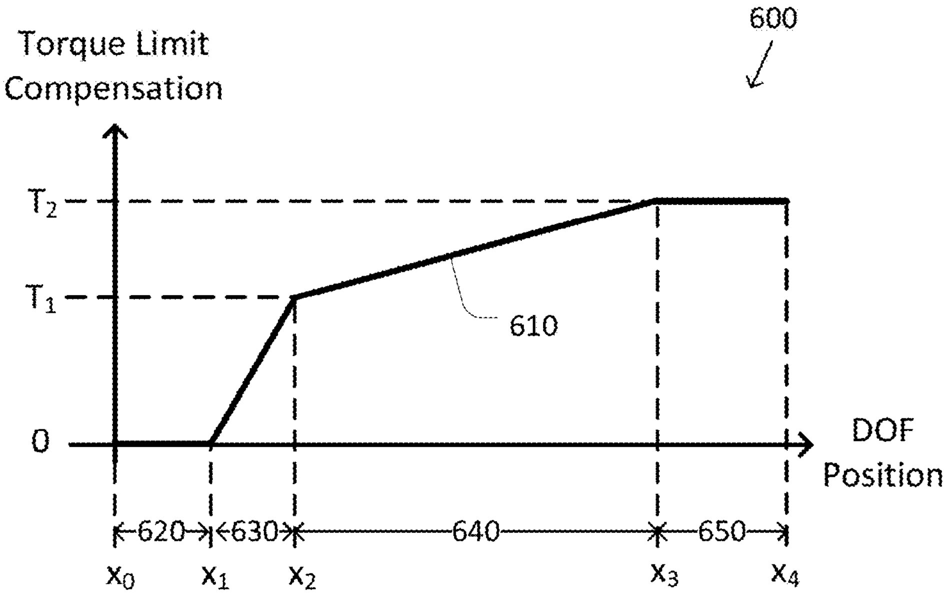
FIG. 6 is a simplified diagram of a torque limit compensation model according to some embodiments.

According to some embodiments, rather than increase force and/or torque limits to compensate for the largest possible restraining and/or return to home force and/or torque, a force and/or torque limit compensation profile may be used that adjusts the force and/or torque limits based on an expected amount of restraining and/or return to home force and/or torque that is being applied by the restraining and/or return to home mechanism. FIG. 6 is a simplified diagram of a torque limit compensation model 600 according to some embodiments. And although model 600 is described in terms of torque limit compensation, one of ordinary skill would understand that the concepts in model 600 may be equally applied to provide force limit compensation. As shown in FIG. 6, torque limit compensation model 600 includes a torque limit compensation curve 610 that indicates an amount that one or more torque limits on a DOF may be increased based on an expected restraining and/or return to home torque. In some examples, the torque limits may include an upper torque limit so that a desired operational margin for the DOF may be maintained against the restraining and/or return to home torque. In some examples, when the torque limits specify a range of torques between a lower and an upper torque limit, the torque limit compensation may be applied to both the lower and upper torque limits. In some examples, the torque limit compensation may be used to create torque limits that are asymmetric so that higher magnitude torque limits are used when the restraining and/or return to home torque is being overcome to further manipulate the DOF and lower magnitude torque limits are used when the restraining and/or return to home torque is aiding manipulation of the DOF. In some examples, a DOF control algorithm using four torque limits (e.g., a positive upper torque limit and a positive lower torque limit for DOF changes against the restraining and/or return to home torque and a negative lower torque limit and a negative upper torque limit for DOF changes aided by the restraining and/or return to home torque) may have each of the four torque limits adjusted by adding the torque limit compensation to each of the four torque limits.

As further shown in FIG. 6, torque limit compensation model 600 and torque limit compensation curve 610 are divided into four general regions: a start-up region 620, a transition region 630, an operational region 640, and a saturation region 650. Each of the regions 620-650 corresponds to a different range in DOF position as denoted by the x axis and the x position values $x_0$, $x_1$, $x_2$, $x_3$, and $x_4$ depicted on model 600. For the purposes of discussing FIG. 6, the position of the DOF will be described relative to an x position of the DOF with more positive positions being in a direction that increases the expected restraining and/or return to home torque, however, one of ordinary skill would understand that the positions for the DOF may be represented using any suitable positional and/or rotational axis, such as a position along an axis defined by groove 320 for cutting blade 330, an angle between jaws 310, an amount of pitch and/or yaw flex in articulated wrist 230, a rotational angle of capstan 510, and/or the like and/or could alternatively be characterized with more negative position values corresponding to the direction that increases the expected restraining and/or return to home torque.

Start-up region 620 corresponds to a range of DOF positions from position $x_0$ to position $x_1$ where no torque limit compensation is applied. In some examples, start-up region 620 may correspond to a range of DOF positions where a restraining and/or return to home mechanism is not applied to the DOF. In the examples of FIG. 5, start-up region 620 may correspond to rotational positions of capstan 510 before second end 560 of torsion spring 540 is moved against stop 570. In some examples, start-up region 620 may correspond and/or be applicable to a DOF where the home position corresponds to position $x_2$ even though the DOF may be actuated past position $x_2$ to position $x_1$, such as with gripper jaws where the home position may correspond to closing the gripper jaws most of the way ($x_2$), but not closing the gripper jaws entirely ($x_1$). In some examples, position $x_1$ may correspond to a zero position and/or a negative position of the DOF, such as a position for a cutting blade within a garage feature where the entrance to the garage feature is position 0. In some examples, a width of start-up region may be varied greatly in range based on the respective DOF with a difference between $x_1$ and $x_0$ being as much as 0.25 radians when DOF position is measured in terms of capstan rotation.

Transition region 630 corresponds to a range of DOF positions from position $x_1$ to position $x_2$ where a rapid increase in torque limit compensation is applied. In some examples, transition region 630 may correspond to a range of DOF positions where a restraining and/or return to home mechanism is transitioning from not being engaged to being engaged. In the examples of FIG. 5, transition region 630 may correspond to rotational positions of capstan 510 just after second end 560 of torsion spring 540 is moved against stop 570. In some examples, a width of transition region 630 may be narrow to reflect a rapid transition from where the restraining and/or return to home mechanism moves from a disengaged position to a position in operational range 640. In some examples, a difference between $x_2$ and $x_1$ may be as small as 0.05 radians or smaller when DOF position is measured in terms of capstan rotation.

Operational region 640 corresponds to a range of DOF positions from position $x_2$ to position $x_3$ where a steady increase in torque limit compensation is applied to compensate for increasing restraining and/or return to home torque being applied by the restraining and/or return to home mechanism. In some examples, operational region 640 may correspond to a range of DOF positions where the restraining and/or return to home mechanism applies a proportional restraining and/or return to home torque with increased DOF position. In the examples of FIG. 5, operational region 640 may correspond to rotational positions of capstan 510 where torsion spring 540 applies increased restraining and/or return to home torque based on a spring constant of torsion spring 540. In some examples, a slope of torque limit compensation curve 610 in operational region 640 may be based on the spring constant of torsion spring 540. In some examples, operational region 640 is typically the largest region to reflect the typically wide operational range of the restraining and/or return to home mechanism. In some examples, a difference between $x_3$ and $x_2$ may be as much as 0.7 radians or more when DOF position is measured in terms of capstan rotation.

Saturation region 650 corresponds to a range of DOF positions from position $x_3$ to at least position $x_4$ where no further increase in torque limit compensation is desired. In some examples, saturation region 650 may correspond to an upper limit in the torque that may be applied by the motor, solenoid, servo, active actuator, hydraulic actuator, pneumatic actuator, and/or the like being used to drive the DOF and/or a limit imposed by a drive unit, drive mechanism, and/or the like. In some examples, $x_4$ may correspond to a maximum DOF position and/or a just past maximum DOF position. In the examples of FIGS. 3 and 4A-4C, $x_4$ may be based on the maximum extension length for cutting blade 330 so that it does not strike the distal end of grooves 320 during a cutting operation, a maximum angle between jaws 310, a maximum pitch and/or yaw flex in articulated wrist 230, and/or the like. In some examples, a difference between $x_4$ and $x_3$ may be as short as 0.15 radians or less when DOF position is measured in terms of capstan rotation.

In some examples, torque limit compensation values $T_1$, $T_2$, and/or $T_3$ may depend significantly on the design and/or configuration of the surgical instrument. In the examples of FIGS. 3, 4A-4C, and 5, $T_1$, $T_2$, and/or $T_3$ may be based on a spring constant of torsion spring 540, practical limits on a corresponding DOF position, a size of a motor, solenoid, servo, active actuator, hydraulic actuator, pneumatic actuator, and/or the like used to drive the DOF, and/or a limit imposed by a drive unit, drive mechanism, and/or the like.

Figure 7:
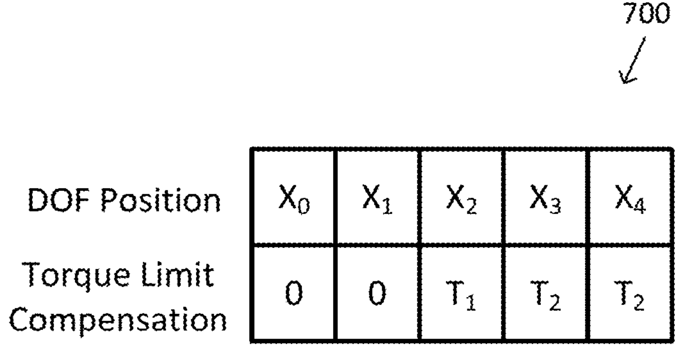
FIG. 7 is a simplified diagram of a lookup table that may be used to characterize the torque limit compensation curve from FIG. 6 according to some embodiments.

FIG. 7 is a simplified diagram of a lookup table 700 that may be used to characterize torque limit compensation curve 610 according to some embodiments. As shown in FIG. 7, lookup table 700 includes a series of control points reflecting the regional boundaries and corresponding torque limit compensation values from torque limit compensation curve. Thus, lookup table 700 includes each of the points $(x_0,0)$, $(x_1,0)$, $(x_2,T_1)$, $(x_3,T_2)$, and $(x_4,T_2)$. Lookup table 700 may be used to support an interpolation and/or other curve fitting algorithm to determine a desired torque limit compensation value based on a current DOF position. In some examples, the interpolation may be linear interpolation based on determining which $x_i$ values the current DOF position is in and using the control points of lookup table 700 to determine the desired torque limit compensation. As an example, consider a case where the current DOF value is $x_c$, where $x_2 \le x_c \le x_3$. In this case, the torque limit compensation, $T_c$, may be computed using Equation 1.

$$T_c = T_1 + \frac{x_c - x_2}{x_3 - x_2}(T_2 - T_1) \qquad \text{Equation 1}$$

In some examples, other interpolation approaches and/or models may be used, including non-linear models, based on the expected restraining and/or return to home behavior of the restraining and/or return to home mechanism. In some examples, the other models may include the use of higher order interpolation polynomials, curve fitting such as cubic splines, and/or the like. In some examples, a complexity of the interpolation model may be selected to balance between computational cost and accuracy of the interpolation model.

As discussed above and further emphasized here, FIGS. 6 and 7 are merely examples which should not unduly limit the scope of the claims. One of ordinary skill in the art would recognize many variations, alternatives, and modifications. According to some embodiments, different torque limit compensation models may be used. In some embodiments, the torque limit compensation curve may be modeled with fewer and/or more control points. In some examples, the torque limit compensation curve may have no start-up region and possibly even a partial transitional region, such as when the restraining and/or return to home mechanism is engaged while the DOF is in the home position. In some examples, this may occur for a cutting blade DOF when it is desired to have the restraining and/or return to home mechanism apply return to home torque when the cutting blade is retracted into the garage feature. In some examples, the torque limit compensation model may reflect symmetry about the home position for DOFs that may be operated in both directions relative to the home position with the torque applied by the restraining and/or return to home mechanism applying return to home torque in both directions about the home position. In some examples, this torque limit compensation model may correspond to an articulated wrist where the pitch and/or yaw DOFs may have a home position with the end effector aligned with the shaft of the surgical instrument. In some examples, the torque limit compensation model may further include hysteresis where a different torque limit compensation curve and/or control points may be used depending on whether the DOF position is increasing or decreasing.

In some embodiments, the torque limit compensation model may support other modeling goals. In some examples, the torque limit compensation model is optional and may not be used for certain operational modes of the end effector or for one or more of the DOFs of the end effector. In some examples, the torque limit compensation model may account for errors in the DOF position caused by bending and/or shifting in the drive mechanisms for the DOF due to flex of the articulated wrist. In some examples, the torque limit compensation curve and/or the control points may vary depending on the surgical instrument and/or the DOF of the surgical instrument for which torque limit compensation is desired. In some examples, lookup tables, such as lookup table 700, may be maintained for each model of surgical instrument and each DOF. In some examples, the lookup tables for each DOF may be determined and/or calibrated separately for each surgical instrument and may be accessible at run time using an identifier, such as a serial number, of the corresponding surgical instrument.

Figure 8:
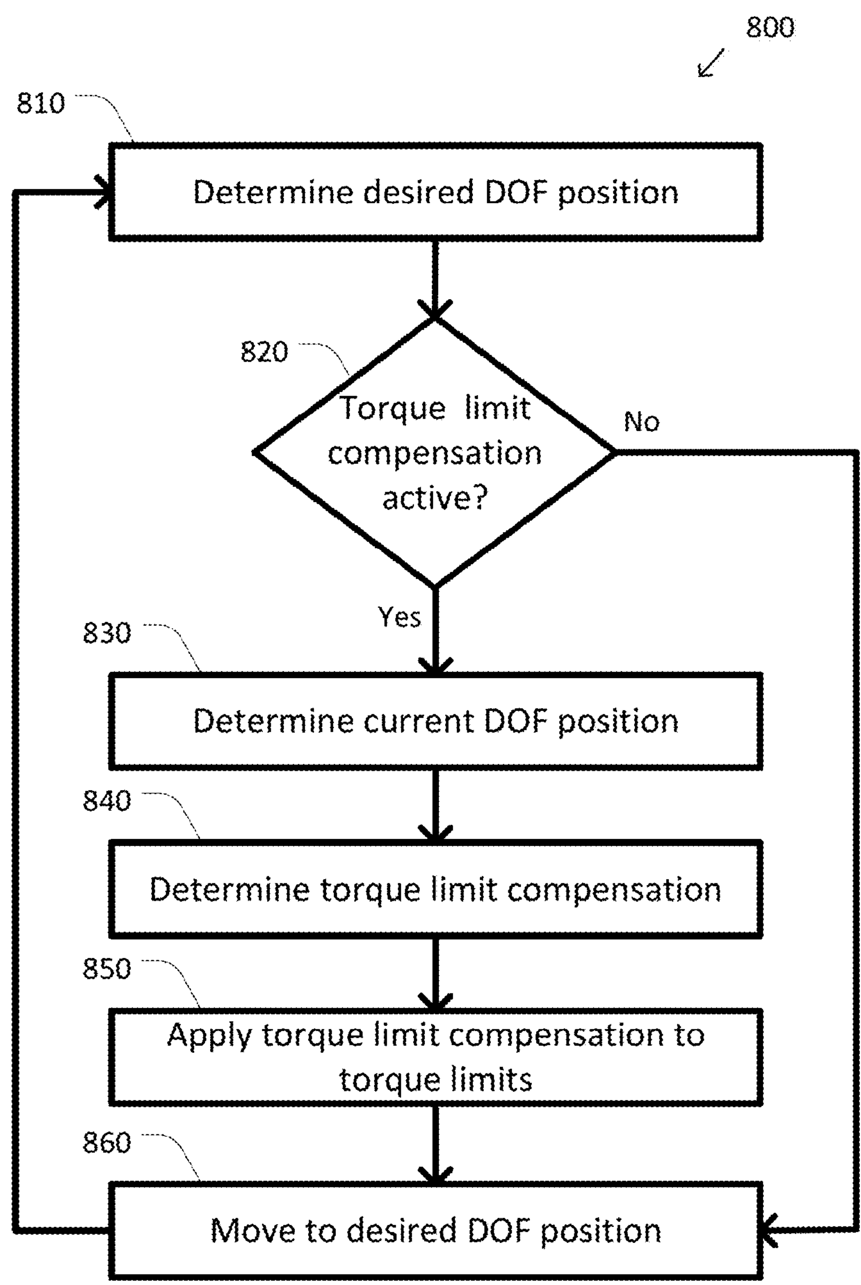
FIG. 8 is a simplified diagram of a method of torque limit compensation according to some embodiments.

FIG. 8 is a simplified diagram of a method 800 of torque limit compensation according to some embodiments. One or more of the processes 810-860 of method 800 may be implemented, at least in part, in the form of executable code stored on non-transient, tangible, machine readable media that when run by one or more processors (e.g., the processor 150 in control unit 140) may cause the one or more processors to perform one or more of the processes 810-860. In some embodiments, method 800 may be performed by an application, such as control application 170. In some embodiments, method 800 may be used to adjust the torque limits of a control algorithm for a DOF in a surgical instrument, such as surgical instrument 200. In some examples, the DOF may correspond to an opening angle of gripper jaws, such as jaws 310, extension and/or retraction of a cutting blade, such as cutting blade 330, flex in an articulated wrist, such as articulated wrist 230, and/or the like. In some embodiments, the torque limit compensation may be modeled based on the torque limit compensation model 600 and/or implemented using a look-up table similar to lookup table 700. In some embodiments, the torque limit compensation may be applied to one or more torque limits for the DOF. In some embodiments, the torque limit compensation may be applied to control algorithms for motors, solenoids, servos, active actuators, hydraulic actuators, pneumatic actuators, and/or the like.

At a process 810, a desired position for a DOF is determined. Based on a control algorithm for the DOF, the desired position for the DOF is determined. In some examples, the desired position for the DOF may correspond to a set point for the DOF. In some examples, the set point may be determined based on inputs received from a surgeon and/or other medical personnel who are operating the surgical instrument, such as surgical instrument 200, to which the DOF belongs. In some examples, the surgeon and/or other medical personnel may manipulate one or more master controls of an operator console, such as one or more master manipulators, levers, pedals, switches, keys, knobs, triggers, and/or the like to teleoperate the DOF. In some examples, the set point for the DOF may be determined based on a positional profile for the DOF as part of an automated and/or semi-automated task that may be triggered by the surgeon and/or other medical personnel. In some examples, the DOF may be associated with a jaw angle of gripper jaws, extension and/or retraction of a cutting blade, flex of a pitch and/or a yaw angle in an articulated wrist, and/or the like.

At a process 820, it is determined whether torque limit compensation is active. Depending upon the DOF and/or a mode of operation of the surgical instrument and/or the end effector, it may not be desirable to use torque limit compensation. In some examples, torque limit compensation may be disabled for each of the DOFs of the surgical instrument and/or selectively activated and/or deactivated individually for each of the DOFs of the surgical instrument.

In some examples, torque limit compensation may be activated and/or deactivated by the surgeon and/or other medical personnel and/or may be activated and/or deactivated by a control application, such as control application 170. In some examples, an indication of whether torque limit compensation is activated and/or deactivated may be determined based on one or more state variables, flags, Boolean values, and/or the like that may be associated with individual degrees of freedom, an end effector as a whole, a surgical instrument as a whole, and/or a computer-assisted device as a whole. When torque limit compensation is not used, torque limits for the DOF may be set to default levels for the DOF and/or default levels for a procedure and/or a task being performed using the surgical instrument. When torque limit compensation is not active, movement of the DOF occurs using a process 860. When torque limit compensation is active, the torque limits for the DOF are adjusted beginning with a process 830.

At the process 830, a current position of the DOF is determined. In some examples, when the amount of restraining and/return to home torque is being compensated for by method 800, the amount of torque limit compensation may be dependent on the current position of the DOF. In the examples, of FIG. 5, the amount of torque applied by torsion spring 540 depends on a rotation angle (equivalent to the DOF position) of capstan 510 and/or shaft 520. In some examples, the DOF position may be measured using one of more position and/or rotation sensors. In some examples, the sensors may be located proximal to the DOF and may be configured to measure the DOF angle indirectly. In some examples, the sensors may be associated with one or more drive units, such as drive unit 500, that may be used to manipulate the DOF. In some examples, the sensors may measure a rotation angle of a capstan, such as capstan 510, and/or a rotation angle of a drive shaft, such as drive shaft 520.

At a process 840, torque limit compensation is determined. A torque limit compensation model, such as torque limit compensation model 600, is used to determine the amount of torque limit compensation to apply based on the current DOF position determined during process 830. In some examples, the torque limit compensation model may account for an expected amount of restraining and/or return to home torque being applied by a restraining and/or return to home mechanism, such as torsion spring 540. In some examples, the torque limit compensation model to use may be selected based on the DOF being moved, a model of the surgical instrument, an identifier of the surgical instrument such as a serial number, and/or the like. In some examples, a torque limit compensation curve, such as torque limit compensation curve 610 may be used to map the current DOF position to the amount of torque limit compensation. In some examples, the torque limit compensation curve may be modeled using a lookup table, such as lookup table 700 with interpolation and/or curve fitting being used to determine the amount of torque limit compensation between entries in the lookup table. In some examples, the interpolation and/or curve fitting may include linear interpolation, polynomial interpolation, cubic spline modeling, and/or the like.

At a process 850, the torque limit compensation is applied to the torque limits. In some examples, one or more of the torque limits for the DOF may be adjusted based on the amount of torque limit compensation determined during process 840. In some examples, the amount of torque limit compensation may be added to each of the torque limits used by the control algorithm for the DOF. In some examples, the torque limits may include an upper torque limit so that a desired operational margin for the DOF may be maintained. In some examples, when the torque limits specify a range of torques between a lower and an upper torque limit, the torque limit compensation may be applied to both the lower and upper torque limits. In some examples, the torque limit compensation may be used to create torque limits that are asymmetric so that higher magnitude torque limits are used when the restraining and/or return to home torque is being overcome to further manipulate the DOF and lower magnitude torque limits are used when the restraining and/or return to home torque is aiding manipulation of the DOF. In some examples, a DOF control algorithm using four torque limits (e.g., a positive upper torque limit and a positive lower torque limit for DOF changes against the restraining and/or return to home torque and a negative lower torque limit and a negative upper torque limit for DOF changes aided by the restraining and/or return to home torque) may have each of the four torque limits adjusted by adding the torque limit compensation to each of the four torque limits.

At the process 860, the DOF is moved to the desired position. In some examples, the DOF is commanded to move to the desired position. In some examples, the DOF may be commanded to move to the desired position by sending one or more signals, such as a voltage, a current, a duty cycle, and/or the like, to a motor, solenoid, servo, active actuator, hydraulic actuator, pneumatic actuator, and/or the like. In some examples, the DOF may be commanded to move to the desired position by applying a torque using a drive component, a drive mechanism, a drive unit, and/or an actuator such as a motor, solenoid, servo, active actuator, hydraulic actuator, pneumatic actuator, and/or the like. In some examples, the amount of torque applied may be limited based on the torque limits determined during process 850 when torque limit compensation is active and/or the default torque limits described previously with respect to process 820 when torque limit compensation is not active.

After the DOF is commanded to move, the move and torque limit compensation may be repeated by returning to process 810. In some examples, the process loop of method 800 may be repeated at regular intervals, such as a control loop rate of the control algorithm for the DOF.

As discussed above and further emphasized here, FIG. 8 is merely an example which should not unduly limit the scope of the claims. One of ordinary skill in the art would recognize many variations, alternatives, and modifications. According to some embodiments, the torque limit compensation may be applied to other than position control algorithms, such as a velocity control algorithm and/or the like. In some examples, when a velocity control algorithm is used, process 810 may be omitted and process 860 may be modified to apply a desired velocity to the DOF position subject to the torque limits set by method 800.

Some examples of control units, such as control unit 140 may include non-transient, tangible, machine readable media that include executable code that when run by one or more processors (e.g., processor 150) may cause the on or more processors to perform the processes of method 800. Some common forms of machine readable media that may include the processes of method 800 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:

a drive unit configured to operate a degree of freedom of an instrument supported by the computer-assisted device; and a control unit configured to:

determine an expected amount of restraining or return to home force or torque applied to the degree of freedom;

determine a force or torque limit compensation based on the expected amount of restraining or return to home force or torque;

alter one or more force or torque limits based on the force or torque limit compensation; and adjust, using the drive unit, the degree of freedom subject to the one or more altered force or torque limits.

2. The computer-assisted device of claim 1, wherein the degree of freedom is associated with:

an angle of gripping jaws of an end effector of the instrument; or an amount of extension of a cutting blade of the end effector; or a flex angle of an articulated wrist coupling the end effector to a shaft of the instrument.

3. The computer-assisted device of claim 1, wherein the expected amount of restraining or return to home force or torque is based on a current position of the degree of freedom.

4. The computer-assisted device of claim 1, wherein the restraining or return to home force or torque is applied by a spring.

5. The computer-assisted device of claim 1, wherein a relationship between the expected amount of restraining or return to home force or torque and the force or torque limit compensation is modeled using a compensation curve.

6. The computer-assisted device of claim 5, wherein the compensation curve includes:

a transition region wherein the compensation curve has a first slope;

an operational region wherein the compensation curve has a second slope smaller than the first slope; and a saturation region wherein the force or torque limit compensation is at a maximum value.

7. The computer-assisted device of claim 6, wherein the compensation curve further includes a start-up region wherein the force or torque limit compensation is zero.

8. The computer-assisted device of claim 5, wherein the compensation curve is symmetric about a home position of the degree of freedom.

9. The computer-assisted device of claim 1, wherein a relationship between the expected amount of restraining or return to home force or torque and the force or torque limit compensation is modeled using a lookup table of control points.

10. The computer-assisted device of claim 1, wherein the one or more force or torque limits are altered by adding the force or torque limit compensation to each of the one or more force or torque limits.

11. The computer-assisted device of claim 1, wherein the one or more force or torque limits include an upper force or torque limit and a lower force or torque limit.

12. A method of operating an instrument supported by a computer-assisted device comprising a drive unit configured to operate a degree of freedom of the instrument, the method comprising:

determining, by a control unit of the computer-assisted device, an expected amount of restraining or return to home force or torque applied to the degree of freedom of the instrument;

determining, by the control unit, a force or torque limit compensation based on the expected amount of restraining or return to home force or torque;

altering, by the control unit, one or more force or torque limits based on the force or torque limit compensation; and adjusting, by the control unit using the drive unit, the degree of freedom subject to the one or more force or torque limits.

13. The method of claim 12, wherein the degree of freedom is associated with:

an angle of gripping jaws of an end effector of the instrument; or an amount of extension of a cutting blade of the end effector; or a flex angle of an articulated wrist coupling the end effector to a shaft of the instrument.

14. The method of claim 12, wherein a relationship between the expected amount of restraining or return to home force or torque and the force or torque limit compensation is modeled using a compensation curve.

15. The method of claim 12, wherein a relationship between the expected amount of restraining or return to home force or torque and the force or torque limit compensation is modeled using a lookup table of control points.

16. The method of claim 12, wherein altering the one or more force or torque limits comprises adding the force or torque limit compensation to each of the one or more force or torque limits.

17. A non-transitory machine-readable medium comprising a plurality of machine-readable instructions which, when executed by a control unit associated with a computer-assisted device comprising a drive unit configured to operate a degree of freedom of an instrument supported by the computer-assisted device, are adapted to cause the control unit to perform a method of operating the instrument, the method comprising:

determining an expected amount of restraining or return to home force or torque applied to a degree of freedom of the instrument;

determining a force or torque limit compensation based on the expected amount of restraining or return to home force or torque;

altering one or more force or torque limits based on the force or torque limit compensation; and adjusting, using the drive unit, the degree of freedom subject to the one or more force or torque limits.

18. The non-transitory machine-readable medium of claim 17, wherein the degree of freedom is associated with:

an angle of gripping jaws of an end effector of the instrument; or an amount of extension of a cutting blade of the end effector; or a flex angle of an articulated wrist coupling the end effector to a shaft of the instrument.

19. The non-transitory machine-readable medium of claim 17, wherein a relationship between the expected amount of restraining or return to home force or torque and the force or torque limit compensation is modeled using:

a compensation curve; or a lookup table of control points.

20. The non-transitory machine-readable medium of claim 17, wherein altering the one or more force or torque limits comprises adding the force or torque limit compensation to each of the one or more force or torque limits.

* * * * *